(12) United States Patent
Klint

(10) Patent No.: US 6,805,676 B2
(45) Date of Patent: Oct. 19, 2004

(54) MANOEUVERABLE GUIDE WIRE AND METHOD OF USING SAME

(75) Inventor: Henrik Sønderskov Klint, Einarsvej (DK)

(73) Assignee: Cook Incorporated, Bloomington (IN)

( * ) Notice: Subject to any disclaimer, the term of this patent is extended or adjusted under 35 U.S.C. 154(b) by 241 days.

(21) Appl. No.: 09/968,763

(22) Filed: Oct. 2, 2001

(65) Prior Publication Data

US 2002/0072689 A1 Jun. 13, 2002

(30) Foreign Application Priority Data

Oct. 3, 2000 (EP) .............................................. 00610104

(51) Int. Cl.$^7$ ................................................. A61B 5/00
(52) U.S. Cl. ........................................................ 600/585
(58) Field of Search ................................ 600/433–435, 600/585; 604/169.13, 523–534

(56) References Cited

U.S. PATENT DOCUMENTS

| 4,676,249 A | 6/1987 | Arenas et al. |
| 4,895,168 A | 1/1990 | Machek |
| 4,932,419 A * | 6/1990 | de Toledo .................... 600/585 |
| 5,807,324 A | 9/1998 | Griffin, III |
| 6,475,209 B1 * | 11/2002 | Larson et al. ............... 604/525 |

FOREIGN PATENT DOCUMENTS

| EP | 0363661 | 4/1990 | |
| EP | 0468645 | 1/1992 | |
| EP | 0860177 | 8/1998 | |
| WO | WO 9213483 A1 * | 8/1992 | ............ A61B/5/00 |
| WO | 0010636 | 3/2000 | |

* cited by examiner

Primary Examiner—Mary Beth Jones
Assistant Examiner—David J. McCrosky
(74) Attorney, Agent, or Firm—Brinks Hofer Gilson & Lione

(57) ABSTRACT

A guide wire (1) including an elongate tubular member with a distal end (3) and a proximal end (4), and at least one core member (2) disposed axially movable within the tubular member. A pre-shaped curved portion (12) on the core member is flexible. The tubular member has a first segment (5) with a rigidity causing a straightening of the curved portion (12) when the latter is positioned within the first segment, and a second segment (9) which is flexible so as to be bent when the curved portion of the core member is positioned within the second segment.

26 Claims, 3 Drawing Sheets

MANOEUVERABLE GUIDE WIRE AND METHOD OF USING SAME

CROSS REFERENCE TO RELATED APPLICATIONS

This application claims priority of European Patent Application Serial No. 00610104.2 filed Oct. 3, 2000 filed in the European Patent Office.

FIELD OF THE INVENTION

The present invention relates to medical devices and more particularly to guide wires for use with vascular medical devices and a method for using same.

BACKGROUND OF THE INVENTION

Guide wires are commonly used in the manoeuvering and placement of catheters and the like within a patient's body. Typically a guide wire is first manipulated through the patient's vasculature to a desired location. The catheter, which has a lumen adapted to receive the guide wire, is advanced over the guide wire to follow it to the desired location. One very common guide wire construction has an elongate, flexible helical coil having a proximal end and a distal end, the latter being inserted into the patient.

One guide wire is known from U.S. Pat. No. 4,895,168 to Schneider Inc., which discloses a movable core guidewire assembly that includes a very flexible casing and a core wire to provide rigidity and steerability. The core wire can be straight throughout its length or it can be of a preformed shape. The casing in itself is very flexible and follows any curvature on the core member.

U.S. Pat. No. 5,807,324 to ProCath Corporation discloses a steerable catheter, which comprises an elongated flexible member and a stylet slidably receivable in a lumen of the flexible member. The stylet can have a bent portion which causes a segment of the flexible member in contact with the same to bend. One disadvantage of this steerable catheter is that the catheter is very flexible, so the stylet alone determines the shape of the catheter, and this shape can only be changed by replacing the stylet with a stylet having another shape.

It is an object of the present invention to provide a guide wire with increased manoeuverability.

SUMMARY OF THE INVENTION

In view of this, the guide wire according to the invention is characterized in that the pre-shaped curved portion is flexible, that the tubular member has segments of different transversal stiffnesses, of which at least one first segment has a rigidity causing a straightening of the curved portion when the latter is positioned within the first segment, and of which at least one second segment is flexible so as to be bent when the curved portion of the core member is positioned within the second segment.

By making the core member with at least one portion, in which the core material has been subjected to permanent deformation to form a pre-shaped, curved portion which is flexible so that it can be resiliently straightened out, and by making the tubular member with at least one first segment, which has less transversal flexibility than the curved portion, and at least one second segment, which has higher transversal flexibility than the curved portion on the core member, it is possible for the operator to easily introduce, modify or remove a curvature on the guide wire, simply by effecting displacements of the core member so that the curved portion is moved between locations in the first and the second segments. When the curved portion is moved into the first segment, the curvature of the core member is reduced or straightened out; and when the curved portion is moved into the second segment, the tubular member is curved by the core member. The curvature of the guide wire is thus controlled by the action of the tubular member on the core member. The curvature of the guide wire is automatically adjusted to the local bending flexibility of the guidewire so that more stiff regions will have less curvature. The soft and flexible segments of the guide wire can be operated to curve by positioning the pre-shaped curved portion of the core member at a desired bend in the path, and then move the tubular member so that the soft second segment is positioned abreast of the curved portion. When the core member is retracted into the first segment, the guide wire is straightened. The easy control over the local curvature of the guide wire and the possibility of advancing the core member through the stiff first segment without causing the guide wire to bend, are advantages which facilitate manoeuvering of the guide wire through tortuous paths.

It is preferred that at least the distal segment of the tubular member is a second segment which yields to the curvature of the curved portion of the core member. When the guide wire is advanced along the desired path, the core member is positioned with the curved portion in a first segment located proximal to the distal segment; and when the desired path exhibits a curvature that is difficult to negotiate, the core member can be advanced into the distal (second) segment and set this in a curvature that facilitates further advancement of the guidewire.

In a preferred embodiment, the second segment has a gradually reduced stiffness towards its distal end. When positioned in a vascular system, forces from the vascular walls act on the tubular member and tend to bend it to conform to the vascular path, and as a consequence the forces required from the core member in order to curve the second segment of the tubular member will vary. The gradual change of stiffness of the second segment allows a finely graduated adjustment of the curvature of the guide wire and furthermore it becomes possible to easily balance out the actions from the vascular wall onto the guide wire. If a slightly less curvature is required, the core member can be slightly retracted to a position where the second segment is slightly more stiff, and vice versa.

In order to obtain maximum curvature of the guidewire, the distal segment can have a distal portion in which the tubular member is fully compliant to the curvature of the pre-shaped, curved portion on the core member. It is preferred that this most soft portion is at the distalmost end of the guidewire so that the guide wire can be set with maximum curvature at entry into branched vessels. When the guide wire has been advanced somewhat into the vascular branch, it also acts to support the branch so that a more stiff portion of the guide wire with less curvature can be advanced into the branch without causing damage. In addition there is obtained the well-known advantage of having an atraumatic distal end on the guide wire.

The distal portion of the tubular member can have a length of more than 15 cm which is typically much longer, such as 5 to 40 times longer, than the length of the curved portion of the core member. The tubular member can be moved forwards and backwards and navigated deeper into the vascular system, while the curved portion is kept stationary with respect to the vascular system and controls the curvature of the guide wire at a fixed position, such as at a branch vessel.

This is in particular an advantage when the guide wire is to be inserted into vessels in soft and fragile tissues, such as at an intracranial access during diagnostic and/or interventional neurological techniques including delivery of contrast fluids, drugs or a vaso-occlusive agent, treatment of tumors, aneurysms, AVS (arterio-venous-shunts), and so forth.

To further improve a gradual change of shape during advancement of the guide wire, the distal segment can have a proximal portion with a length of at least 6 cm in which the transversal stiffness of the tubular member is higher than in the distal portion and lower than in the first segment.

It is possible according to the present invention to provide the tubular member with more than one soft second segment in order to allow for controlled navigation through at least two consecutive difficult passages.

The tubular member can have at least two of the first segments and at least two of the second segments, one of the first segments being interposed between the second segments. The separation between the two second segments is fully controlled by the length of the first segment.

The inner member can be movable with respect to the tubular member along a longer distance than half the length of the second segment. This inner member can be positioned fully retracted into a first segment and it can also be fully advanced into the second segment to the position at least at the middle thereof.

The core member can be manufactured with longitudinally separated regions of different stiffnesses, and thus it can be adapted to special situations where the guide wire is designed to be utilized for catheterization of a vasculature of a predetermined configuration.

In an embodiment which is in particular suitable with fully compliant second segments of extended lengths, the core member comprises two elements, which can be axially displaced in relation to each other. These two core elements can be used to adjust the transverse forces required to reduce the curvature of the guide wire in the area of the curved portion. Such a core member is thus adjustable according to needs.

In a further development of this embodiment, a straight section of the one element is movable between positions abreast of and apart from a pre-shaped curved portion on the other element. The straight section of the one element can be used to partially straighten the curvature on the other element and thus modify the effect of the core member on the tubular member.

Although the tubular member can be constructed in many ways satisfying the requirements for segments with adequate transversal stiffness to straighten the inner member, a preferred embodiment is distinguished by the tubular member comprising a multifilar helically wound row of wires, and that the row wires is made up of from 2 to 12 helically wound wires, preferably of from 4 to 8 helically wound wires. Due to the very high flexibility, pushability and torqueability and the ability of the construction to maintain each of these three characteristics even when set in a very tortuous pattern involving two or more tight loops, the guide wire can be of use in very small and distant vessels such as deep brain sites accessed by intracranial catheterization. By using several wires in the row, their aggregate width can be adapted to correspond to the desired pitch for the given diameter of the guide wire. A row of more than 12 wires has a tendency to buckle when the wires are helically wound in the common winding operation. For wires of round cross-sectional shape, a number of from 4 to 8 wires in the row is preferred; but for flat wires or wires of oval shape, two or three wires in a row can be more suitable.

It is an advantage that the wires have a pitch angle in the range of 26°–76°, preferably a pitch angle in the range of 40°–65°. Although it is possible to use other pitch angles, angles chosen in these ranges provide a balanced solution to the requirements for the desired high flexibility, high column strength and fine torqueability. The inner range of 40°–65° is in particular useful for advancing the guide wire to very distant, small sized vessels, such as in blood vessels in the brain, whereas the subrange of 35°–40° is applicable when very high flexibility is a dominant requirement, and the subrange of 70°–76° is applicable when very high pushability is a dominant requirement. It is of course possible to choose different pitch angles in different segments of the tubular body.

Preferably, the wires in the row are machined to a lesser outer diameter, such as by grinding, in the second segment (s) of the tubular member. Grinding is a process that allows precision manufacturing of the guide wires with customized transverse flexibility.

One manner of providing the guide wire with the second portions is to machine the distal segment to a tapering shape with decreasing outer diameter in the distal direction.

Preferably, the guide wire has a 30 cm long distal segment having a maximum outer diameter of less than 0.75 mm which makes it very suitable for intracranial operation.

In a further development the tubular member is open in its proximal end and closed in its distal end.

The present invention furthermore relates to a method to advance a guide wire along a path which presents a localized directional change. The method is characterized in that a pre-shaped curved portion of a core member is positioned at the localized directional change in the path, whereafter a tubular member of the guide wire is advanced over the core member while the latter is kept stationary in relation to the localized directional change. The pre-shaped curved portion acts on the tubular member and provides the guidewire with a curvature or bend which, during advancement of the tubular member, is mainly stationary with respect to the localized directional change in the path.

BRIEF DESCRIPTION OF THE DRAWING

In the following, examples of embodiments of the invention are described in more detail with reference to the highly schematic drawing, in which.

DETAILED DESCRIPTION OF THE INVENTION

Figure 1:
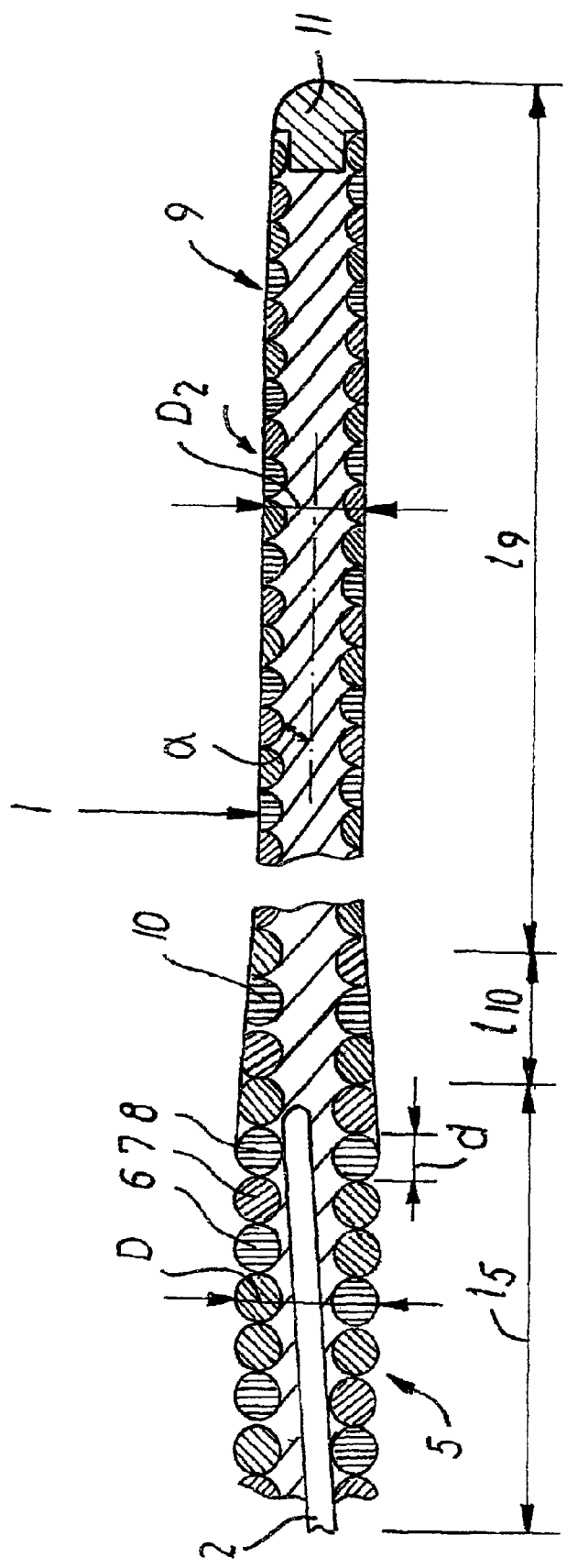
FIG. 1 is a longitudinal sectional view of the distal end of the guide wire according to the invention.

In the following description of embodiments, the same reference numerals are used for features of the same type.

The guide wire depicted in FIG. 1 comprises an elongate tubular member 1 and a stylet-like core member 2 which is preferably solid and placed within the tubular member. The tubular member has a distal end 3 capable of being advanced to a target site in the vascular system and a proximal end 4

(FIG. 6) that is kept outside the patient's body. A first segment 5 extends from the proximal end towards the distal end and carries near the proximal end a traditional torquer (not shown) releasably secured onto the guidewire. The guidewire can typically have a length in the range of 50–300 cm and a maximum outer diameter D in the range of 0.204–1.072 mm (0.008–0.042 inches).

The wires 6, 7, 8 of the tubular member are of a linear elastic material, such as stainless steel, titanium or tantalum, or they are made of a superelastic alloy, such as nitinol. The diameter d of the wire is in the range of 0.06–0.45 mm, and preferably in the range of 0.15–0.35 mm. In case the wire is of stainless steel, the wire preferably has an ultimate tensile strength in the range of 1800–2700 N/mm$^2$, but lower or higher values are also possible. The tubular member is preferably made by placing a group of from two to twelve wires, preferably three or four wires, in a row next to each other, e.g., according to the desired pitch angle α, whereafter the group of wires is wound about a mandrel. Then the mandrel with the coiled wires can be subjected to heat treatment in order to remove residual stresses from the wires. As an example the heat treatment can last for about two hours in an oven at a temperature of about 500° C. After the heat treatment the mandrel is removed from the wires.

The tubular member has a second segment 9 located distally of the first segment 5. The second segment has the same inner diameter, but a smaller outer diameter D2 than the first segment so that the second segment has substantially lower transversal stiffness than the first segment. A tapered section 10 can be used to connect the first and second segments. The variation of diameter of the tubular member can be produced by using wires of different diameter, but it is preferred to make the entire tubular member of continuous wires of even dimensions and then make the reduced diameter in the second segments by grinding the outside of the tubular member in a centerless grinding machine.

As mentioned above the smaller outer diameter in the second segment(s) results in considerably larger transverse flexibility and higher softness, but torque is nevertheless transferred fully to the distal end of the guide wire.

The tubular member is open ended at the proximal end and it can also be open ended at the distal end, but preferably it is made with a closed distal end. The end closure can be made by mounting a distal end member 11 onto the tubular member. End member 11 has an atraumatic front end termination, such as a rounded front or a front of very flexible material or very flexible configuration. End member 11 can be solder, or a sphere that can be for example laser welded onto the distal end of the tubular member. Further, end member 11 can also include a soft coil of radiopaque material, or it can be coated with a radiopaque material, e.g., gold.

Figure 4:
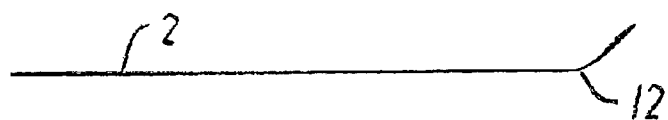

The core member 2 is made of a linearly elastic material, such as stainless steel, titanium or tantalum, or it is made of a superelastic alloy, such as nitinol. The diameter d of the wire is in the range of 0.05–0.50 mm, and preferably in the range of 0.10–0.35 mm. The core member has at least one pre-shaped curved portion 12 (FIG. 4). The core member is flexible and in the area of the curved portion 12, the core member has a transverse stiffness that is higher than the transverse stiffness of the second segment 9, but lower than the transverse stiffness of the first segment 5. It is preferred that the stiffnesses of the first and second segments deviate at least 30% from the stiffness of the core member.

Figure 2A:
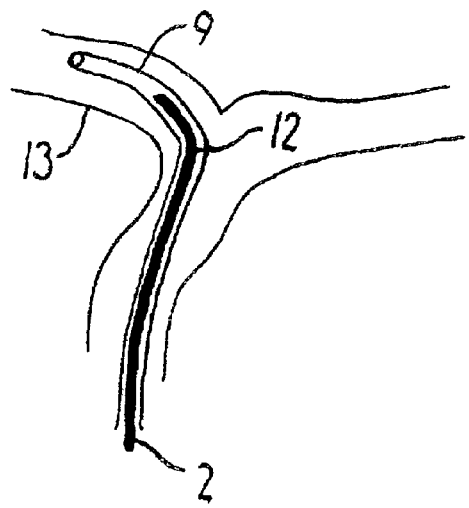
FIGS. 2a, 2b and 2c are sketches of the guide wire at a bend.
Figure 2B:
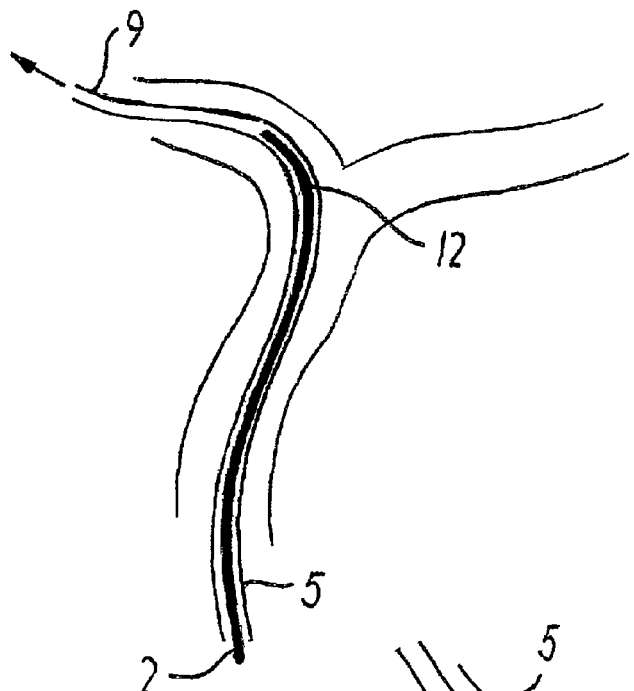
Figure 2C:
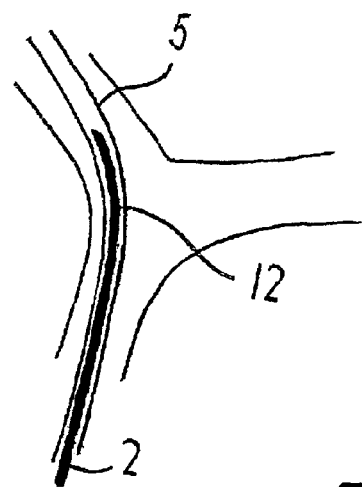

FIGS. 2a–2c illustrate advancement of the guide wire past a localized directional change in the vascular path at a branch vessel 13. Firstly, the guide wire is advanced to a position close to the branch vessel while the core member is located with the curved portion 12 inside a first segment 5, and then the core member is displaced with respect to the tubular member until the curved portion is located inside a second segment 9 which compliantly is curved by curved portion 12 as depicted in FIG. 2a. Next, the core member is held in position with curved portion 12 at the localized directional change and the tubular member is pushed forwards further into branch vessel 13 as indicated in FIG. 2b. At the continued advancement of the tubular member, the more rigid first segment is advanced up past the curved portion 12 which causes the curved portion to be flexibly straightened as is depicted in FIG. 2c. At this point the guide wire has been deeply advanced along the path on the distal side of branch vessel 13 so that the guide wire interacts with the vasculature without causing trauma. The core member can then be advanced in the distal direction to a new location where the procedure can be repeated.

Figure 3:
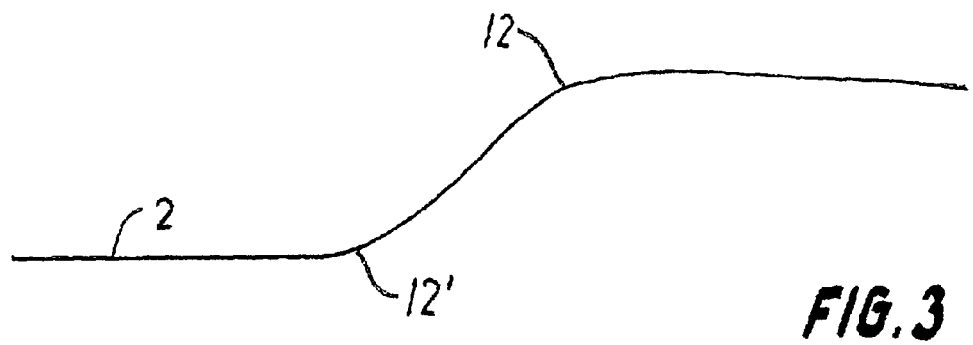
FIGS. 3 and 4 illustrate two embodiments of a core member of the guide wire.
Figure 5A:
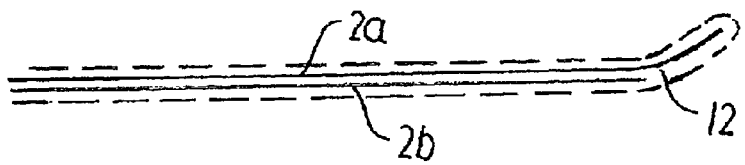
FIGS. 5a and 5b illustrate a core member comprising two elements.
Figure 5B:
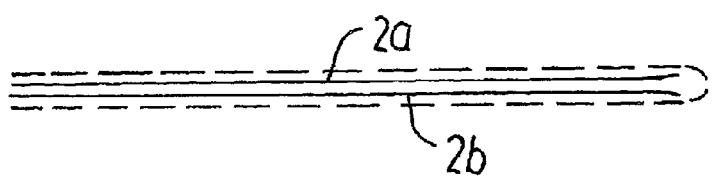

The core member 2 can have more than one pre-shaped curved portion, such as two curved portions 12, 12' located a predetermined distance apart as illustrated in FIG. 3. In the above mentioned embodiments, the core member is constituted by a single, solid rod or stylet. In an alternative embodiment depicted in FIGS. 5a and 5b, the core member includes two elements 2a, 2b, of which one element 2a has a curved portion 12 like in the embodiment of FIG. 4, whereas the other element 12b is straight at a location corresponding to 12. When the other element 12b is retracted somewhat in relation to the first element, curved portion 12 is free to act on the tubular member and bend the second segment thereof (FIG. 5a). When the other element 12b is moved in the distal direction, its straight portion is positioned abreast of curved portion 12 and here it influences the tubular member and counteracts the bending action of the curved portion with the result that the second segment is straightened (FIG. 5b). This composite core member is in particular useful in connection with very soft and very long second segments because the segment can be advanced in the vascular system with the core member in position inside the second segment, but with an inactivated curved portion. When the second segment is positioned at a bend in the path, element 1b can be retracted somewhat to activate the curved portion so that the second segment assumes a bent configuration.

Figure 6:
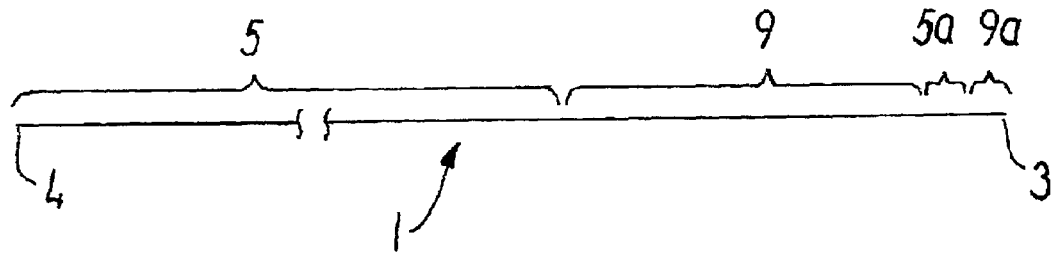
FIG. 6 illustrates a guide wire having two first segments and two second segments.

In the embodiment of FIG. 6, the tubular member has a proximal first segment 5 followed by a second segment 9 which in the vicinity of the distal end is followed by a first segment 5a which is followed by a very soft second segment 9a. The distal first segment 5a has a length which is only slightly longer that the curved portion 12 on the core member and it serves to straighten curved portion 12 when this is desired.

In order to facilitate mutual movement of the core member and the tubular member, the outside of the core member and/or the inside of the tubular member can be provided with a layer or coating of a low friction material, e.g., polytetrafluoroethylene (PTFE), to minimize the force necessary to push, pull or torque the core member in the tubular member and facilitate advancement or twisting of the core member in the tubular member.

The various embodiments can be combined into other embodiments within the scope of the present invention.

What is claimed is:

1. A guide wire comprising:
    an elongate tubular member with a distal end and a proximal end, and at least one core member disposed axially movable within the tubular member, which core member is provided with at least one pre-shaped, curved portion, wherein the pre-shaped curved portion is flexible, and the tubular member has segments of different transversal stiffnesses, of which at least one first segment has a rigidity causing a straightening of said curved portion when the latter is positioned within said first segment, and of which at least one second segment is flexible so as to be bent when said curved portion of the core member is positioned within said second segment, wherein the second segment is a distal segment of the tubular member, the distal segment having a distal portion in which the tubular member is fully compliant to the curvature of the pre-shaped curved portion on the core member, the distal portion having a length of more than 15 cm, the distal segment including a proximal portion having a length of at least 6 cm in which the transversal stiffness is higher than in the distal portion and lower than in the first segment, wherein the tubular member has at least two of the first segments and at least two of the second segments, one of the first segments being interposed between the second segments.

2. A guide wire according to claim 1, wherein the second segment has a gradually reduced stiffness towards its distal end.

3. A guide wire according to claim 1, wherein the tubular member is open in its proximal end and closed in its distal end.

4. A guide wire according to claim 3, wherein the inner member is movable with respect to the tubular member along a longer distance than half the length of the second segment.

5. A guide wire according to claim 4, wherein distalmost second segment of the tubular member has a length of at least 15 cm.

6. A guide wire according to claim 5, wherein the core member has longitudinally separated regions of different stiffnesses.

7. A guide wire according to claim 6, wherein the core member comprises two elements, which can be axially displaced in relation to each other.

8. A guide wire according to claim 7, wherein a straight section of the one element is moveable between positions abreast of and apart from a pre-shaped curved portion on the other element.

9. A guide wire according to claim 8, wherein the tubular member comprises a multifilar helically wound row of wires, and that the row of wires is made of from 2 to 12 helically wound wires, preferably of from 4 to 8 helically wound wires.

10. A guide wire according to claim 9, wherein the wires have a pitch angle in the range of 26°–76°, preferably a pitch angle in the range of 40°–65°.

11. A guide wire according to claim 9, wherein the wires in said row are machined to a lesser outer diameter in the second segment or segments of the tubular member.

12. A guide wire according to claim 11, wherein said distal segment is machined to a tapering shape with decreasing outer diameter in the distal direction.

13. A guide wire according to claim 12, wherein the guide wire has a 30 cm long distal segment having a maximum outer diameter of less than 0.75 mm.

14. A guide wire comprising:
an elongate tubular member with a distal end and a proximal end, and at least one core member disposed axially movable within the tubular member, which core member is provided with at least one pre-shaped, curved portion, wherein the pre-shaped curved portion is flexible, and the tubular member has segments of different transversal stiffnesses, of which at least one first segment has a rigidity causing a straightening of said curved portion when the latter is positioned within said first segment, and of which at least one second segment is flexible so as to be bent when said curved portion of the core member is positioned within said second segment, wherein the second segment is a distal segment of the tubular member, the distal segment having a distal portion in which the tubular member is fully compliant to the curvature of the pre-shaped curved portion on the core member, the distal segment having a proximal portion in which the transversal stiffness is higher than in the distal portion and lower than in the first segment, wherein the tubular member has at least two of the first segments and at least two of the second segments, one of the first segments being interposed between the second segments.

15. A guide wire according to claim 14, wherein the second segment has a gradually reduced stiffness towards its distal end.

16. A guide wire according to claim 14, wherein the tubular member is open in its proximal end and closed in its distal end.

17. A guide wire according to claim 16, wherein the inner member is movable with respect to the tubular member along a longer distance than half the length of the second segment.

18. A guide wire according to claim 17, wherein distalmost second segment of the tubular member has a length of at least 15 cm.

19. A guide wire according to claim 18, wherein the core member has longitudinally separated regions of different stiffnesses.

20. A guide wire according to claim 19, wherein the core member comprises two elements, which can be axially displaced in relation to each other.

21. A guide wire according to claim 20, wherein a straight section of the one element is moveable between positions abreast of and apart from a pre-shaped curved portion on the other element.

22. A guide wire according to claim 21, wherein the tubular member comprises a multifilar helically wound row of wires, and that the row of wires is made of from 2 to 12 helically wound wires, preferably of from 4 to 8 helically wound wires.

23. A guide wire according to claim 22, wherein the wires have a pitch angle in the range of 26°–76°, preferably a pitch angle in the range of 40°–65°.

24. A guide wire according to claim 23, wherein the wires in said row are machined to a lesser outer diameter in the second segment or segments of the tubular member.

25. A guide wire according to claim 24, wherein said distal segment is machined to a tapering shape with decreasing outer diameter in the distal direction.

26. A guide wire according to claim 25, wherein the guide wire has a 30 cm long distal segment having a maximum outer diameter of less than 0.75 mm.

* * * * *